(12) United States Patent
Henry

(10) Patent No.: US 7,589,194 B2
(45) Date of Patent: Sep. 15, 2009

(54) CRYSTALLINE K-252B, SODIUM SALT, METHANOLATE PENTAHYDRATE

(75) Inventor: Rodger F. Henry, Wildwood, IL (US)

(73) Assignee: Abbott Laboratories, Abbott Park, IL (US)

( * ) Notice: Subject to any disclaimer, the term of this patent is extended or adjusted under 35 U.S.C. 154(b) by 62 days.

(21) Appl. No.: 11/972,293

(22) Filed: Jan. 10, 2008

(65) Prior Publication Data

US 2008/0171868 A1 Jul. 17, 2008

Related U.S. Application Data

(60) Provisional application No. 60/885,016, filed on Jan. 16, 2007.

(51) Int. Cl.
*C07D 498/18* (2006.01)

(52) U.S. Cl. ...................................... 540/545

(58) Field of Classification Search .................. 540/545
See application file for complete search history.

*Primary Examiner*—Bruck Kifle
(74) *Attorney, Agent, or Firm*—Andrew M. Parial

(57) ABSTRACT

A crystalline (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-k1]pyrrolo[3,4-i][1,6]benzodiazocin-1-one methanolate pentahydrate and ways to make it are disclosed.

1 Claim, No Drawings

CRYSTALLINE K-252B, SODIUM SALT, METHANOLATE PENTAHYDRATE

This application claims priority to U.S. Provisional application Ser. No. 60/885,016, filed Jan. 16, 2007.

FIELD OF THE INVENTION

This invention pertains to a crystalline sodium (9S-(9α, 10β,12α))-2,3,9,10,11,12-hexahydro-10-hydroxy-10-(carboxylate)-9-methyl-9,12-epoxy-1H-diindolo[1,2,3-fg:3',2', 1'-kl]pyrrolo[3,4-i][1,6]benzodiazocin-1-one methanolate pentahydrate and ways to make it.

BACKGROUND OF THE INVENTION

Because the relationship between different crystalline forms of intermediates, and solvates thereof, in processes to make drugs may provide guidance for further development, there is an existing need in the chemical process and therapeutic arts for identification of different crystalline forms of the intermediates, or the solvates thereof, and ways to reproducibly make them.

SUMMARY OF THE INVENTION

One embodiment of this invention, therefore, pertains to crystalline sodium (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one methanolate pentahydrate characterized in the monoclinic crystal system and $P2_1$ space group, when measured at about −100° C. with Mo—Kα radiation, by lattice parameters a, b and c of 13.200 Å±0.003 Å, 6.938 Å±0.003 Å and 15.617 Å±0.007 Å, respectively, and β of 104.674°±0.007.

Still another embodiment pertains to a process for making crystalline sodium (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one comprising:

making and isolating or not isolating (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one;

providing a mixture comprising water, methanol and the sodium (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one, wherein the sodium (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one is completely dissolved in the water;

causing sodium (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one methanolate pentahydrate to exist in the mixture, wherein the sodium (9S-(9α,10β,12α))-2,3,9,10,11, 12-hexahydro-10-hydroxy-10-(carboxylate)-9-methyl-9,12-epoxy-1H-diindolo[1,2,3-fg:3',2',1'-kl]pyrrolo[3,4-i][1,6] benzodiazocin-1-one methanolate pentahydrate, when isolated and measured in the monoclinic crystal system and $P2_1$ space group at about −100° C. with Mo—Kα radiation, is characterized by lattice parameters a, b and c of 13.200 Å±0.003 Å, 6.938 Å±0.003 Å and 15.617 Å±0.007 Å, respectively, and β of 104.674°±0.007; and isolating the sodium (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one methanolate pentahydrate.

Sodium (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one methanolate pentahydrate prepared as described in the preceding process.

DETAILED DESCRIPTION OF THE INVENTION

The synthesis of sodium (9S-(9α,10β,12α))-2,3,9,10,11, 12-hexahydro-10-hydroxy-10-(carboxylate)-9-methyl-9,12-epoxy-1H-diindolo[1,2,3-fg:3',2',1'-kl]pyrrolo[3,4-i][1,6] benzodiazocin-1-one is described in U.S. Pat. No. 4,923,986.

This invention pertains to discovery of sodium (9S-(9α, 10β,12α))-2,3,9,10,11,12-hexahydro-10-hydroxy-10-(carboxylate)-9-methyl-9,12-epoxy-1H-diindolo[1,2,3-fg:3',2', 1'-kl]pyrrolo[3,4-i][1,6]benzodiazocin-1-one methanolate pentahydrate, ways to make it having substantial crystalline, chemical and diastereomeric purity, ways to characterize it, compositions containing it and methods of treatment of diseases and inhibition of adverse physiological events using it.

The term "amorphous," as used herein, means a supercooled liquid or a viscous liquid which looks like a solid but does not have a regularly repeating arrangement of molecules that is maintained over a long range and does not have a melting point but rather softens or flows above its glass transition temperature.

The term "anti-solvent," as used herein, means a solvent in which a compound is substantially insoluble.

The term "sodium (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one methanolate pentahydrate," as used herein, means sodium (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one with one methanol and five water solvate molecules.

The term "crystalline," as used herein, means having a regularly repeating arrangement of molecules or external face planes.

The term "isolating" as used herein, means separating a compound from a solvent, anti-solvent, or a mixture of solvent and anti-solvent to provide a solid, semisolid or syrup. This is typically accomplished by means such as centrifugation, filtration with or without vacuum, filtration under positive pressure, distillation, evaporation or a combination thereof. Isolating may or may not be accompanied by purifying during which the chemical, chiral or chemical and chiral purity of the isolate is increased. Purifying is typically conducted by means such as crystallization, distillation, extraction, filtration through acidic, basic or neutral alumina, filtration through acidic, basic or neutral charcoal, column chromatography on a column packed with a chiral stationary phase, filtration through a porous paper, plastic or glass barrier, column chromatography on silica gel, ion exchange chromatography, recrystallization, normal-phase high performance liquid chromatography, reverse-phase high performance liquid chromatography, trituration and the like.

The term "miscible," as used herein, means capable of combining without separation of phases.

The term "solvate," as used herein, means having on a surface, in a lattice or on a surface and in a lattice, a solvent such as water, acetic acid, acetone, acetonitrile, benzene, chloroform, carbon tetrachloride, dichloromethane, dimethylsulfoxide, 1,4-dioxane, ethanol, ethyl acetate, butanol, tert-butanol, N,N-dimethylacetamide, N,N-dimethylformamide, formamide, formic acid, heptane, hexane, isopropanol, methanol, methyl ethyl ketone, 1-methyl-2-pyrrolidinone, mesitylene, nitromethane, polyethylene glycol, propanol, 2-propanone, pyridine, tetrahydrofuran, toluene, xylene, mixtures thereof and the like. A specific example of a solvate is a hydrate, wherein the solvent on the surface, in the lattice or on the surface and in the lattice, is water. Hydrates may or may not have solvents other than water on the surface, in the lattice or on the surface and in the lattice of a substance.

The term "supersaturated," as used herein, means having a compound in a solvent in which it is completely dissolved at a certain temperature but at which the solubility of the compound in the solvent at that certain temperature is exceeded.

Unless stated otherwise, percentages stated throughout this specification are weight/weight (w/w) percentages.

Causing sodium (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one methanolate pentahydrate to exist in a mixture comprising sodium (9S-(9α,10β,12α))-2,3,9,10,11,12-hexahydro-10-hydroxy-1,0-(carboxylate)-9-methyl-9,12-epoxy-1H-diindolo[1,2,3-fg:3',2',1'-kl]pyrrolo[3,4-i][1,6]benzodiazocin-1-one, methanol and water, wherein the sodium (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one is completely dissolved in the water and the methanol, is nucleation. In a preferred embodiment for the practice of this invention, nucleation of sodium (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one methanolate pentahydrate is made to occur in methanol and water which is supersaturated with sodium (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one.

For the practice of this invention, nucleation may be made to occur in a solution by techniques that are well-known to those skilled in the art such as, for example, solvent removal, temperature change, solvent-miscible anti-solvent addition, solvent-immiscible anti-solvent addition, chafing or scratching the interior of the container, preferably a glass container with a glass rod or a glass bead or beads, or by a combination thereof.

It is meant to be understood that, because many solvents and anti-solvents contain impurities, the level of impurities in solvents and anti-solvents for the practice of this invention, if present, are at a low enough concentration that they do not interfere with the intended use of the solvent in which they are present.

EXAMPLE 1

(9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one methanolate pentahydrate A mixture of (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one and methanol and water in which the (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one was partially soluble in the water was warmed to 50° C. until the 9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one completely dissolved, cooled to ambient temperature and filtered.

The foregoing is meant to be illustrative of the invention and not meant to limit it to disclosed embodiments. Variations and changes obvious to one skilled in the art are intended to be within the scope and nature of the invention as defined in the appended claims.

What is claimed is:

1. Crystalline (9S-(9α,10β,12α))-2,3,9,10,11,12-hexahydro-10-hydroxy-10-(carboxylate)-9-methyl-9,12-epoxy-1H-diindolo[1,2,3-fg:3',2',1'-kl]pyrrolo[3,4-i][1,6]benzodiazocin-1-one methanolate pentahydrate characterized in the monoclinic crystal system and $P2_1$ space group, when measured at about −100° C. with Mo-Kα radiation, by lattice parameters a, b and c of 13.200 Å±0.003 Å, 6.938 Å±0.003 Å and 15.617 Å±0.007 Å, respectively, and β of 104.674°±0.007.

* * * * *